(12) United States Patent
Kerr (10) Patent No.: US 9,113,938 B2
(45) Date of Patent: Aug. 25, 2015

(54) APPARATUS FOR PERFORMING ELECTROSURGICAL PROCEDURES HAVING A SPRING MECHANISM ASSOCIATED WITH THE JAW MEMBERS

(75) Inventor: Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 778 days.

(21) Appl. No.: 13/228,742

(22) Filed: Sep. 9, 2011

(65) Prior Publication Data

US 2013/0066318 A1    Mar. 14, 2013

(51) Int. Cl.
| A61B 18/14 | (2006.01) |
| A61B 17/29 | (2006.01) |
| A61B 17/28 | (2006.01) |
| A61B 18/00 | (2006.01) |
| A61B 17/00 | (2006.01) |
| A61B 19/00 | (2006.01) |

(52) U.S. Cl.
CPC ............ *A61B 17/29* (2013.01); *A61B 18/1442* (2013.01); *A61B 2017/003* (2013.01); *A61B 2017/2845* (2013.01); *A61B 2017/2926* (2013.01); *A61B 2017/2932* (2013.01); *A61B 2017/2936* (2013.01); *A61B 2018/0063* (2013.01); *A61B 2018/00577* (2013.01); *A61B 2018/00589* (2013.01); *A61B 2018/00595* (2013.01); *A61B 2018/00601* (2013.01); *A61B 2018/00607* (2013.01); *A61B 2018/1412* (2013.01); *A61B 2018/1455* (2013.01); *A61B 2019/302* (2013.01)

(58) Field of Classification Search
USPC ..................................... 606/51–52
See application file for complete search history.

(56) References Cited

U.S. PATENT DOCUMENTS

| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,009,661 A | 4/1991 | Michelson |

(Continued)

FOREIGN PATENT DOCUMENTS

| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Paula J Stice (57) ABSTRACT

An end effector assembly is presented including a pair of first and second jaw members configured to move from a first position in spaced relation relative to one another to a second position for grasping tissue therebetween. The end effector assembly further includes an actuation mechanism configured to actuate the first and second jaw members relative to an elongated shaft attached to a flexible catheter having a longitudinal axis defined therethrough. Additionally, a spring mechanism is disposed between a supporting member and a distal most end of the elongated shaft, the spring mechanism configured to apply constant sealing pressure between the first and second jaw members irrespective of angular displacement of the elongated shaft.

20 Claims, 5 Drawing Sheets

(56) References Cited

U.S. PATENT DOCUMENTS

| | | |
|---|---|---|
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,562,699 A | 10/1996 | Heimberger et al. |
| D384,413 S | 9/1997 | Zlock et al. |
| H1745 H | 8/1998 | Paraschac |
| 5,827,271 A | 10/1998 | Buysse et al. |
| D402,028 S | 12/1998 | Grimm et al. |
| D408,018 S | 4/1999 | McNaughton |
| D416,089 S | 11/1999 | Barton et al. |
| 6,033,399 A | 3/2000 | Gines |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,398,779 B1 | 6/2002 | Buysse et al. |
| H2037 H | 7/2002 | Yates et al. |
| D465,281 S | 11/2002 | Lang |
| D466,209 S | 11/2002 | Bon |
| 6,585,735 B1 | 7/2003 | Frazier et al. |
| D493,888 S | 8/2004 | Reschke |
| 6,796,981 B2 | 9/2004 | Wham et al. |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,090,673 B2 | 8/2006 | Dycus et al. |
| D531,311 S | 10/2006 | Guerra et al. |
| D533,274 S | 12/2006 | Visconti et al. |
| D533,942 S | 12/2006 | Kerr et al. |
| 7,150,097 B2 | 12/2006 | Sremcich et al. |
| 7,150,749 B2 | 12/2006 | Dycus et al. |
| D535,027 S | 1/2007 | James et al. |
| 7,156,846 B2 | 1/2007 | Dycus et al. |
| 7,179,258 B2 | 2/2007 | Buysse et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,597,693 B2 | 10/2009 | Garrison |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2 | 8/2010 | Hixson et al. |
| 7,771,425 B2 | 8/2010 | Dycus et al. |
| 7,780,662 B2 | 8/2010 | Bahney |
| 7,799,028 B2 | 9/2010 | Schechter et al. |
| D627,462 S | 11/2010 | Kingsley |
| D628,289 S | 11/2010 | Romero |
| D628,290 S | 11/2010 | Romero |
| 7,857,812 B2 | 12/2010 | Dycus et al. |
| D630,324 S | 1/2011 | Reschke |
| 7,951,150 B2 | 5/2011 | Johnson et al. |
| 7,963,965 B2 | 6/2011 | Buysse et al. |
| 2002/0188294 A1 | 12/2002 | Couture et al. |
| 2003/0032956 A1 | 2/2003 | Lands et al. |
| 2003/0229344 A1 | 12/2003 | Dycus et al. |
| 2004/0087943 A1 | 5/2004 | Dycus et al. |
| 2004/0249374 A1 | 12/2004 | Tetzlaff et al. |
| 2005/0137592 A1 | 6/2005 | Nguyen et al. |
| 2005/0250989 A1 | 11/2005 | Suzuki |
| 2006/0189980 A1 | 8/2006 | Johnson et al. |
| 2006/0217697 A1 | 9/2006 | Lau et al. |
| 2007/0142834 A1 | 6/2007 | Dumbauld |
| 2007/0260242 A1 | 11/2007 | Dycus et al. |
| 2008/0319442 A1 | 12/2008 | Unger et al. |
| 2009/0012520 A1 | 1/2009 | Hixson et al. |
| 2009/0112229 A1* | 4/2009 | Omori et al. .................. 606/130 |
| 2009/0149854 A1* | 6/2009 | Cunningham et al. .......... 606/51 |
| 2009/0171350 A1 | 7/2009 | Dycus et al. |
| 2009/0182327 A1 | 7/2009 | Unger |
| 2009/0209960 A1 | 8/2009 | Chojin |
| 2009/0248021 A1 | 10/2009 | McKenna |
| 2009/0259224 A1 | 10/2009 | Wham et al. |
| 2010/0076430 A1 | 3/2010 | Romero |
| 2010/0076433 A1* | 3/2010 | Taylor et al. ..................... 606/52 |
| 2010/0094289 A1 | 4/2010 | Taylor et al. |
| 2010/0145334 A1 | 6/2010 | Olson et al. |
| 2010/0179539 A1 | 7/2010 | Nau, Jr. |
| 2010/0179545 A1 | 7/2010 | Twomey et al. |
| 2011/0054469 A1 | 3/2011 | Kappus et al. |
| 2011/0106079 A1 | 5/2011 | Garrison et al. |
| 2012/0191090 A1* | 7/2012 | Sugahara et al. ............... 606/45 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026 179 | 12/2005 |
| DE | 20 2007 009 165 | 10/2007 |
| DE | 20 2007 009 317 | 10/2007 |
| DE | 20 2007 016 233 | 3/2008 |
| DE | 19738457 | 1/2009 |
| DE | 10 2008 018 406 | 7/2009 |
| EP | 1159926 | 12/2001 |
| EP | 2147652 A1 | 1/2010 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2004-517668 | 6/2004 |

(56) References Cited

FOREIGN PATENT DOCUMENTS

| JP | 2004-528869 | 9/2004 |
|---|---|---|
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |
| WO | 2011043126 A1 | 4/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, 6/920/00, Thomas P. Ryan.
U.S. Appl. No. 12/336,970, filed Dec. 17, 2008, Paul R. Sremeich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, filed Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/719,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.

(56) References Cited

OTHER PUBLICATIONS

Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.

Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'L Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.

(56) References Cited

OTHER PUBLICATIONS

Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
PCT International Search Report, for International Application No. PCT/US2012/052738, dated Dec. 26, 2012.
Supplementary European Search Report for EP 12 82 9765 dated Apr. 15, 2015.

* cited by examiner

FIG. 9

APPARATUS FOR PERFORMING ELECTROSURGICAL PROCEDURES HAVING A SPRING MECHANISM ASSOCIATED WITH THE JAW MEMBERS

BACKGROUND

1. Technical Field

The present disclosure relates to an apparatus for performing a surgical procedure and, more particularly, to an electrosurgical apparatus including an end effector having a pair of jaw members for providing a mechanical advantage at the end effector.

2. Background of Related Art

Electrosurgical instruments, e.g., electrosurgical endoscopic forceps, are well known in the medical arts and typically include a housing, a handle assembly, a shaft and an end effector assembly attached to a distal end of the shaft. The end effector includes jaw members configured to manipulate tissue. Typically, the electrosurgical instrument is operatively and selectively coupled to an RF power source that is in operative communication with a control system for performing an electrosurgical procedure. Electrosurgical endoscopic forceps utilize both mechanical clamping action and electrical energy to effect hemostasis by heating tissue and blood vessels to coagulate, cauterize, seal, cut, desiccate, and/or fulgurate tissue.

Typically, the jaw members include a highly conductive seal plate and are pivotably coupled to one another via one or more mechanical interfaces that provide a point of pivot for one or both jaw members. For example, in certain instances, a cam slot including a cam pin operably disposed therein and a pivot pin are operably coupled to the end effector and/or one or both jaw members. In this instance, the cam slot, cam pin and pivot pin collectively pivot and close one or both jaw members. For added structural integrity, the cam slot, cam pin and pivot pin are fabricated from metal.

In certain instances, to facilitate moving the jaw members from an open position for grasping tissue to a closed position for clamping tissue (or vice versa) such that a consistent, uniform tissue effect (e.g., tissue seal) is achieved, one or more types of suitable devices are operably associated with the electrosurgical endoscopic forceps. For example, in some instances, one or more types of springs, e.g., a compression spring, are operably coupled to the handle assembly associated with the electrosurgical endoscopic forceps. In this instance, the spring is operatively associated with a drive assembly to facilitate actuation of a movable handle associated with the handle assembly to ensure that a specific closure force between the jaw members is maintained within one or more suitable working ranges.

In certain instances, the shaft bends or deforms during the course of an electrosurgical procedure. For example, under certain circumstances, a clinician intentionally bends or articulates the shaft to gain mechanical advantage at the surgical site. Or, under certain circumstances, the surgical environment causes unintentional or unwanted bending or flexing of the shaft, such as, for example, in the instance where the shaft is a component of a catheter-based electrosurgical endoscopic forceps. When the shaft is bent or deformed, there are frictional losses associated with a drive wire or cable translating through the shaft from the spring in the housing, which, in turn, diminishes, impedes and/or prevents effective transfer of the closure force that is needed at the jaw members. Moreover, the frictional losses also lessen the operative life of the spring, which, in turn, ultimately lessens the operative life of the surgical instrument. The spring allows for more flexibility when passing through curves in the catheter.

An increased mechanical advantage and/or mechanical efficiency with respect to transferring the closure force(s) from the handle assembly to the jaw members may prove advantageous in the relevant art.

SUMMARY

In accordance with one aspect of the present disclosure, an end effector assembly is provided. The end effector assembly includes a pair of first and second jaw members configured to move from a first position in spaced relation relative to one another to a second position for grasping tissue therebetween. The end effector assembly further includes an actuation mechanism configured to actuate the first and second jaw members relative to an elongated shaft attached to a catheter having a longitudinal axis defined therethrough. Additionally, a spring mechanism is disposed between a supporting member and a distal most end of the elongated shaft, the spring mechanism configured to apply constant sealing pressure between the first and second jaw members inespective of angular displacement of the elongated shaft.

In accordance with another aspect of the present disclosure, the first position defines a gap between the supporting member and the distal most end of the elongated shaft. In accordance with yet another aspect of the present disclosure, the elongated shaft and the catheter are bendable or flexible and the actuation mechanism includes at least one drive element.

In accordance with another aspect of the present disclosure, a cam pin is mounted by the supporting member, which rides on a cam slot in the first jaw member, such that the first jaw member closes with respect to the second jaw member. The cam slot is disposed at an angle relative to the longitudinal axis defined by the elongated shaft. The actuation mechanism causes a camming member to be slidably received within a cavity of the second jaw member to allow reception of the cam pin.

In accordance with yet another aspect of the present disclosure, the spring mechanism is selected from a group including a coil spring, and a cantilever spring. The spring mechanism is rated at less than 120 pounds per square inch. The spring mechanism provides a closure force of about 3 $kg/cm^2$ to about 16 $kg/cm^2$ between the pair of jaw members.

In accordance with a second aspect of the present disclosure, a tissue contacting surface of one of the first and second jaw members includes a cutting assembly. A second actuation mechanism actuates the cutting assembly to slidingly advance across the tissue contacting surface of the second jaw member along the longitudinal axis defined by the elongated shaft to cut tissue disposed between the pair of jaw members.

In accordance with another aspect of the present disclosure, an end effector assembly is provided. The end effector assembly includes a pair of first and second jaw members configured to move from a first position in spaced relation relative to one another to a second position for grasping tissue therebetween. An actuation mechanism is configured to actuate the first and second jaw members relative to an elongated shaft attached to a catheter having a longitudinal axis defined therethrough. A spring mechanism is disposed between a supporting member and a distal most end of the elongated shaft, the spring mechanism configured to apply constant sealing pressure between the first and second jaw members irrespective of angular displacement of the elongated shaft. Additionally, a cam slot is configured to cooperate with the supporting member to receive a cam pin therethrough.

In this description reference is made to bendable members. These members are also referred to as turnable members or flexible members. In the descriptions set out herein, terms such as "bendable section," "bendable segment," "bendable motion member," or "turnable member" refer to an element of the instrument that is controllably bendable in comparison to an element that is pivoted at a joint. The bendable elements of the present disclosure enable the fabrication of an instrument that bends in any direction without any singularity and that is further characterized by a ready capability to bend in any direction, all with a single unitary or uni-body structure. A definition of these bendable motion members may be: an instrument element, formed either as a controller or something that is controlled, and that is capable of being constrained by tension or compression forces to deviate from a straight line to a curved configuration without any sharp breaks and/or angularity.

In the figures and in the description that follows, in which like reference numerals identify similar or identical elements, the term "proximal" refers to the end of the apparatus which is closest to the operator during use, while the term "distal" refers to the end which is farthest from the operator, as is traditional.

BRIEF DESCRIPTION OF THE DRAWINGS

Various embodiments of the presently disclosed surgical instrument or end effector assembly are described hereinbelow with references to the drawings, wherein.

DETAILED DESCRIPTION OF THE EMBODIMENTS

Further scope of applicability of the present disclosure will become apparent from the detailed description given hereinafter. However, it should be understood that the detailed description and specific examples, while indicating particular embodiments of the present disclosure, are given by way of illustration only, since various changes and modifications within the spirit and scope of the present disclosure will become apparent to those skilled in the art from this detailed description.

Detailed embodiments of the present disclosure are disclosed herein; however, the disclosed embodiments are merely exemplary of the disclosure, which is embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

With reference to FIGS. 1-9, illustrative embodiments of end effector assemblies 100, 200, 300, 400, 500 associated with an electrosurgical apparatus (not shown) for performing an electrosurgical procedure are shown. In the exemplary embodiments, the end effector assemblies are operatively and selectively coupled to an electrosurgical generator (not shown) for performing an electrosurgical procedure. Alternatively, the end effector assemblies may be battery-powered. An electrosurgical procedure includes sealing, cutting, cauterizing coagulating, desiccating, and/or fulgurating tissue all of which employ RF energy. The generator is configured for monopolar and/or bipolar modes of operation. The generator includes or is in operative communication with a system (not shown) that includes one or more processors in operative communication with one or more control modules that are executable on the one or more processors.

Turning now to FIGS. 1-3 and 7, end effector assembly 100 includes opposing jaw members 10, 20 that mutually cooperate to grasp, seal and, in some eases, divide tubular vessels and vascular tissues. The pair of opposing jaw members 10, 20 cooperates with or is operatively associated with supporting member 30. First jaw member 10 cooperates with supporting member 30 via cam slot 36. Cam slot 36 is configured to receive cam pin 34 to allow the pair of opposing jaws 10, 20 to move relative to each other. The pair of opposing jaw members 10, 20 further include pivot pin 32 for securing the pair of opposing jaw members 10, 20 to each other. Supporting member 30 is configured to operatively cooperate with elongated shaft 60 via one or more cables 40 and spring mechanism 50. In general, as mentioned above, end effector assembly 100 is configured to be operatively associated with or operatively communicate with any type of surgical instrument having any type of handle assembly and any type of energizing means.

Figure 1:
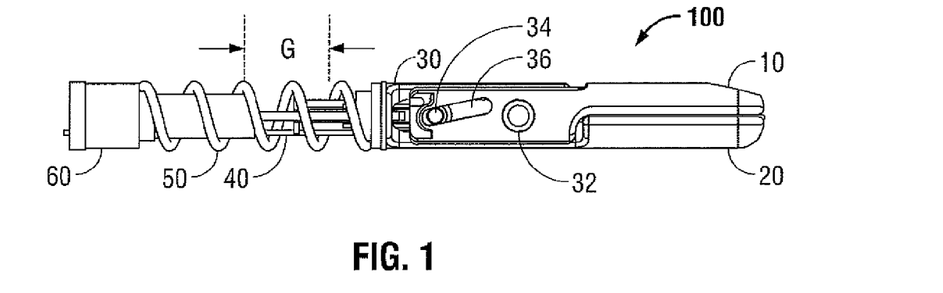
FIG. 1 is a side view of an end effector assembly, with a pair of jaw members shown in a closed position, in accordance with a first embodiment of the present disclosure.
Figure 2:
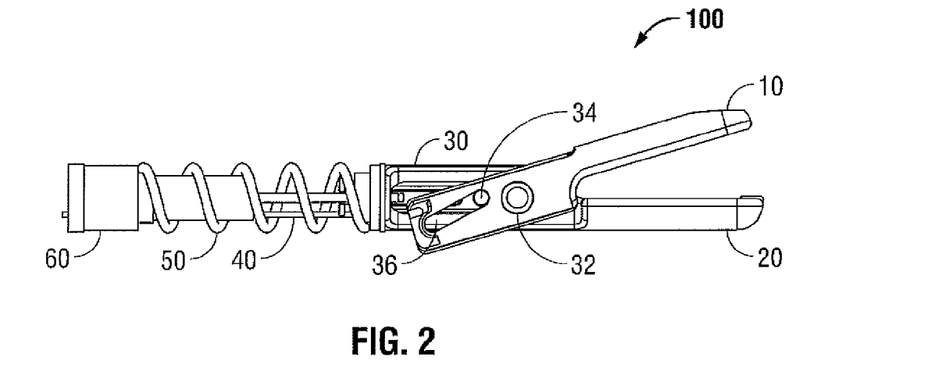
FIG. 2 is a side view of the end effector assembly, with the pair of jaw members shown in an open position, in accordance with the first embodiment of the present disclosure.
Figure 3:
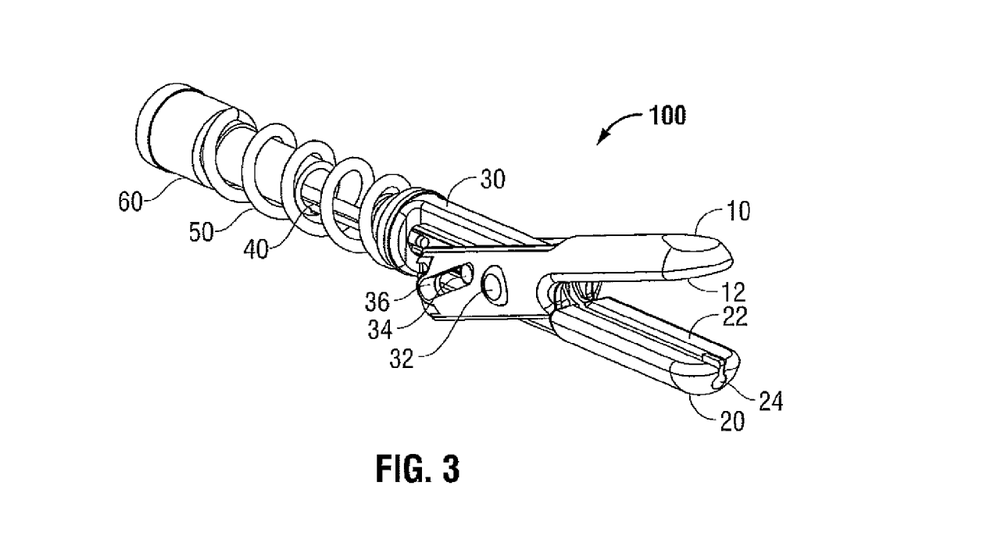
FIG. 3 is a perspective, front view of the end effector assembly, with the pair of jaw members shown in the open position, in accordance with the first embodiment of the present disclosure.
Figure 4:
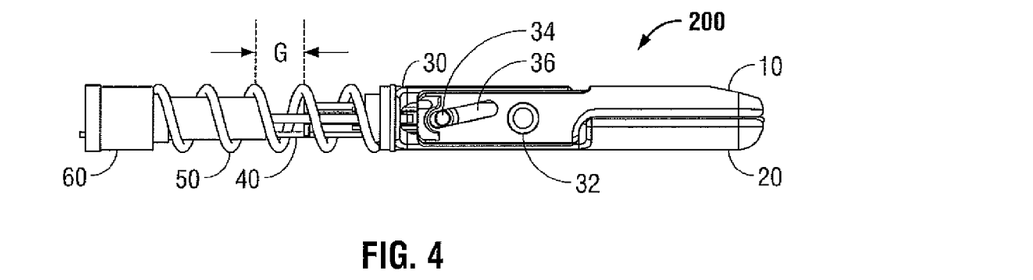
FIG. 4 is a side view of the end effector assembly, with the pair of jaw members shown in the closed position, where a cutting knife assembly is not exposed, in accordance with a second embodiment of the present disclosure.
Figure 5:
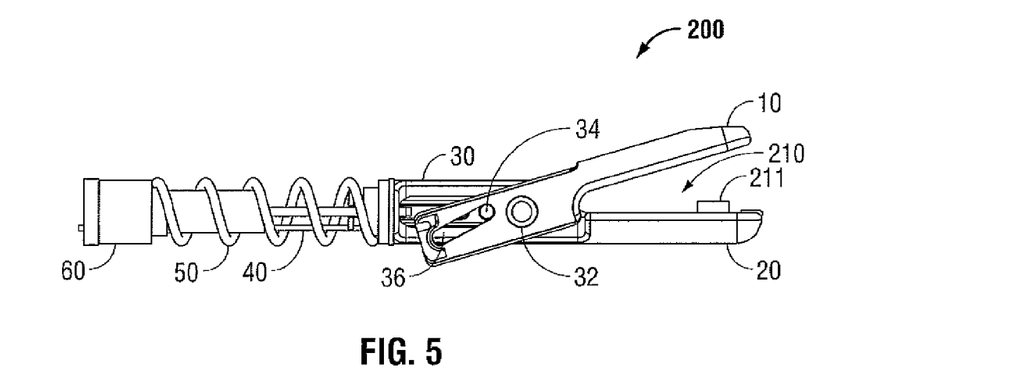
FIG. 5 is a side view of the end effector assembly, with the pair of jaw members shown in the open position, where the cutting knife assembly is exposed, in accordance with the second embodiment of the present disclosure.

In FIG. 1, jaw members 10, 20 are shown in a first position or closed position. In FIGS. 2 and 3, jaw members 10, 20 are shown in a second position or an open position. In the closed position, first and second jaw members 10, 20 cooperate to perform one or more of the following: grasp, cauterize, cut, and seal tissue. First jaw member 10 includes tissue contacting surface 12 that opposes a corresponding tissue contacting surface 22 on second jaw member 20. Second jaw member 20 also includes one or more stop members 24.

Additionally, first jaw member 10 is movable, whereas second jaw member 20 is stationary (unilateral jaw design). Alternatively, both first jaw member 10 and second jaw member 20 may be movable relative to each other (bilateral jaw design). Any type of suitable movable/stationary configuration for jaw members 10, 20 may be constructed.

Proximal end of first jaw member 10 includes a generally rectangular configuration including a cam slot 36 defined therein that includes geometry of suitable proportion to securely affix first jaw member 10 to second jaw member 20. In the embodiments illustrated in FIGS. 1-3, 7, and 9, cam slot 36 includes a generally oval or elliptical configuration defined by a generally oval sidewall having four generally arcuate corners. More particularly, cam slot 36 includes a generally oval configuration having a height, length and width each proportioned.

A portion of proximal end of first jaw member 10 is operably secured to supporting member 30, which acts as a rigid center post. To this end, supporting member 30 is made from a non-conductive (or partially conductive) material. Suitable materials that supporting member 30 is formed from include but are not limited to plastic, ceramic, metals, metal alloys, and so forth.

In operation, supporting member 30 is in operative communication with one or more cables 40 forming a drive element 520 (see FIG. 9) of a drive assembly or actuation mechanism (not shown) such that movement of the drive element 520 causes one or both jaw members 10, 20 to move from the opened position to the closed or clamping position. Thus, the actuation mechanism is a drive element 520 having one or more cables 40. For example, in one particular embodiment, when the drive element 520 is "pulled," i.e., moved or translated proximally, one or both jaw members 10, 20 is/are caused to move toward each other. In an alternate embodiment, when the drive element 520 is "pushed," i.e., moved or translated proximally, one or both jaw members 10, 20 are caused to move toward each other. In certain instances, it is useful to have a drive element 520 and/or one or more cables 40 that are flexible. The one or more cables 40 extend from the proximal-most end of elongated shaft 60 to jaw members 10, 20 via supporting member 30.

A portion of first jaw member 10 further defines cam slot 36 and a pivot pin opening 33 (see FIG. 7) each configured such that one or both jaw members 10, 20, e.g., jaw member 10, pivots with respect to the other jaw member, e.g., jaw member 20, while providing electrical insulation for cam slot 36 and pivot pin 32 from one or more electrical components associated with one or both jaw members 10, 20. Pivot pin 32 need not be preloaded since pivot pin 32 is not in tension under the present structural configuration of placing spring mechanism 50 directly next to jaw members 10, 20. Additionally, by not preloading pivot pin 32, frictional losses are reduced.

Therefore, as seen in FIG. 1, the closure force is the spring force until the one or more cables 40 of drive element 520 (see FIG. 9) bottom out. In other words, the drive element 520 gets pulled against the force of the spring mechanism 50 and closes the gap "G." When the drive element 520 bottoms out against the stop member 24 (see FIG. 3), an appropriate sealing pressure is applied to the pair of jaw members 10, 20. Additionally, the cam pin 34 is mounted by supporting member 30, which rides on the cam slot 36 of the first jaw member 10, such that the first and second jaw members 10, 20 are in a closed position.

Spring mechanism 50 may be, a coil spring and a cantilever spring. In one embodiment, spring mechanism 50 is rated at less than 120 pounds per square inch and is configured to provide a closure force of about 3 kg/cm$^2$ to about 16 kg/cm$^2$.

Figure 9:
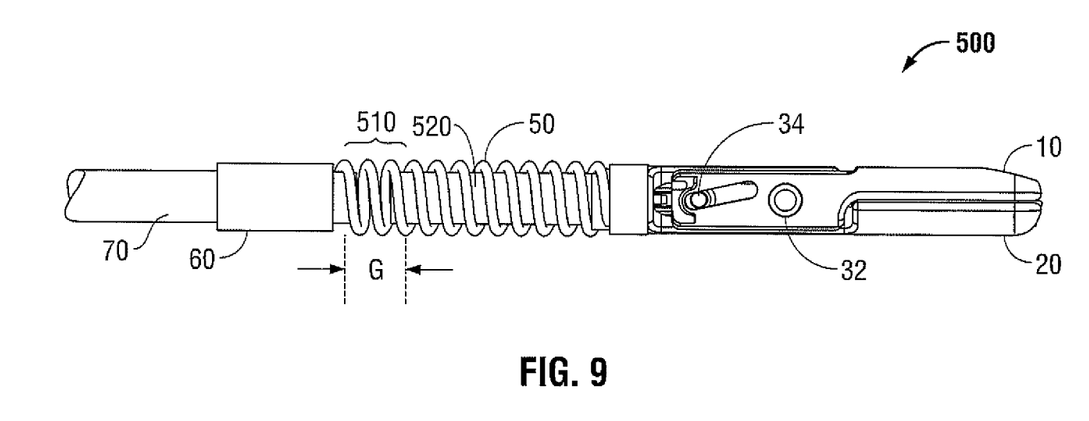
FIG. 9 is a side view of the end effector assembly, with the pair of jaw members shown in the closed position, where a gap "G" is depicted when the jaw members are not latched, in accordance with the present disclosure.

Elongated shaft 60 may be attached to a flexible or bendable catheter 70 (see FIG. 9). There are several advantages brought forth by employing bendable sections for elongated shaft 60 particularly as opposed to other mechanisms such as pivotal joints or ball-and-socket joints. One attribute of the bendable member, especially for bending in two degrees of freedom is uniformity in bending. Because the bendable member bends in any direction uniformly, it has no inherent singularity, and as a result, the operator produces uniform rolling motion of the tool, an important motion for tasks such as suturing, simply by rolling the control handle. On the other hand, if motion members are comprised of series of pivotal joints, not only does it bind due to singularities, but the rolling of the control handle results in unwanted side motion of the tool as well, thus affecting its usability for surgical procedure(s).

In use, initially jaw members 10, 20 are in an open position. For example, tissue is positioned between jaw members 10, 20 and, subsequently, a movable handle (not explicitly shown) is moved to cause one or more cables 40 of the drive element 520 (see FIG. 9) to move proximally. Proximal movement of the drive element 520 causes cam pin 34 positioned within cam slot 36 associated with jaw member 10 to move proximally, which, in turn, causes one or both jaw members, e.g., jaw member 10, to move toward the other jaw member, e.g., jaw member 20, such that tissue is clamped between jaw members 10, 20. Thus, the closure force is the spring force until the drive element 520 bottoms out.

Furthermore, with reference to FIG. 9, gap 510 is shown, in a configuration 500 where jaw members 10, 20 are not latched for seal pressure. Drive element 520 pulls cam pin 34. Drive element 520 is then pulled against a force of spring 50 and closes gap 510. When drive element 520 bottoms out against stop members 24, 230, the appropriate sealing pressure is applied to jaw members 10, 20. FIGS. 1-3, 7, and 9 depict jaw members 10, 20 being in a closed position, but not latched for seal pressure, since drive element 520 has been pulled against the force of spring mechanism 50. In such configurations, the sealing pressure applied to jaws 10, 20 may be suitable for the intended application. Thus, when gap 510 is closed, proper sealing pressure is applied even after jaw members 10, 20 go around one or more corners (which creates frictional losses). In contrast, when gap 510 is present, jaw members 10, 20 are not yet latched for seal pressure.

Spring mechanism 50 is positioned between supporting member 30 and a distal-most end of elongated shaft 60, such that sealing forces applied to first and second jaw members 10, 20 are offloaded by the spring mechanism 50 independent of movement of elongated shaft 60. In other words, by locating jaw members 10, 20 directly adjacent spring mechanism 50, instead of the handle assembly (not shown), one or more cables 40 extending the length of elongated shaft 60 experience some minimal frictional losses due to the bending of elongated shaft 60. But those frictional losses do not affect the sealing pressure between jaw members 10, 20. Thus, the spring mechanism 50 is configured to adjust sealing pressure of the first and second jaw members 10, 20, while the first and second jaw members 10, 20 are angularly displaced during advancement of the catheter 70 (see FIG. 9) within a subject.

Spring mechanism 50 is typically preloaded to provide for suitable stiffness and for the most suitable jaw closing forces. As a result, suitable jaw forces or seal pressure is entirely independent of the longitudinal axis or longitudinal path defined by elongated shaft 60. Therefore, frictional losses due to bending of elongated shaft 60 are minimized due to the positioning of spring mechanism 50 closer to jaw members 10, 20. Further, the drive element may be overloaded so that any frictional losses in the drive element 520 do not affect the required forces necessary to effect a seal (by virtue of spring mechanism 50 regulating the closure forces).

Consequently, spring mechanism 50 does not bias jaw members 10, 20. In such a structural configuration, as described in the example embodiments, jaw members 10, 20 are biased solely by the one or more cables 40 or drive element 520 that is in operative communication with supporting member 30, which, in turn, imparts energy for movement of jaw members 10, 20 in relation to each other via cam slot 36 and cam pin 34.

In a second embodiment 200 of the present disclosure, referring to FIGS. 4-6 and 8, cutting assembly 210 (see FIG. 6) is provided. Cutting assembly 210 includes knife 211 and is positioned on tissue contacting surface 22 of second jaw member 20. The actuation mechanism that includes cables 40 actuates cutting assembly 210 to slidingly advance knife 211 across tissue contacting surface 22 along recessed path 220 (see FIG. 6) that is parallel to the longitudinal axis of elongated shaft 60.

Thus, cutting assembly 210 is disposed between opposing jaw members 10, 20 of end effector assembly 200. Cutting assembly 210 and end effector assembly 200 are independently operable relative to one another, e.g., a trigger assembly (not shown) actuates cutting assembly 210 and handle assembly (not shown) actuates end effector assembly 200. Cutting assembly 210 is generally cut in a progressive, unidirectional fashion (e.g., distally), however, cutting assembly 210 may be configured to cut bi-directionally depending upon a particular purpose.

Cutting assembly 210 also includes a locking mechanism (not explicitly shown) for preventing actuation of knife 211 in any place across the length of tissue contacting surface 22. Cutting assembly 210 is also fully or partially disposed within supporting member 30. Also, cutting assembly 210 may or may not be insulated.

Additionally, at least one jaw member, e.g., second jaw member 20, includes one or more stop member 230 (see FIG. 6), that limit(s) the movement of the two opposing jaw members 10, 20 relative to one another. Stop member 230 extends from tissue contacting surface 22 a predetermined distance according to the specific material properties (e.g., compressive strength, thermal expansion, etc.) to yield a gap distance during sealing (e.g., between about 0.001 inches to about 0.006 inches). Stop member 230 is made from an insulative material, e.g., parylene, nylon and/or ceramic and are configured to limit opposing movement of jaw members 10, 20 to within the above mentioned gap range or other suitable gap. Stop member 230 may be disposed one or both jaw members 10, 20.

Figure 6:
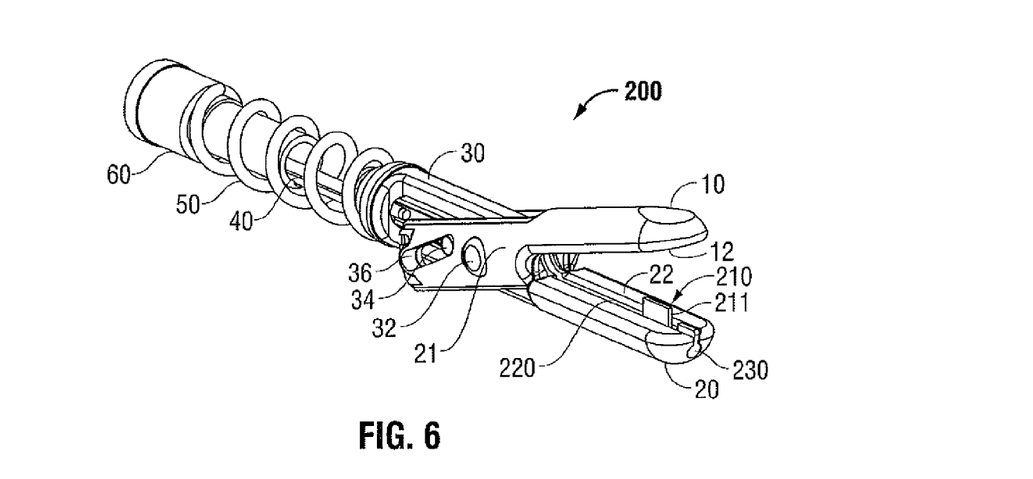
FIG. 6 is a perspective, front view of the end effector assembly, with the pair of jaw members shown in the open position, where the cutting knife assembly is exposed, in accordance with the second embodiment of the present disclosure.
Figure 7:
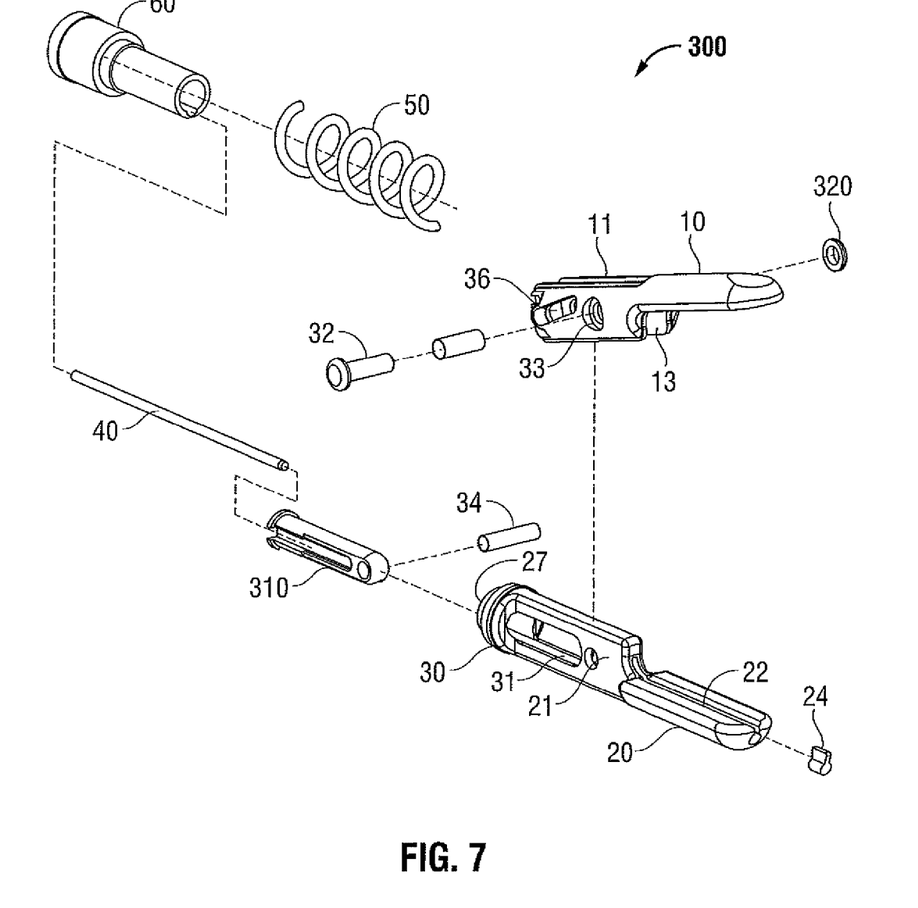
FIG. 7 is an exploded view of the end effector assembly of FIG. 3 with parts separated, in accordance with the present disclosure.
Figure 8:
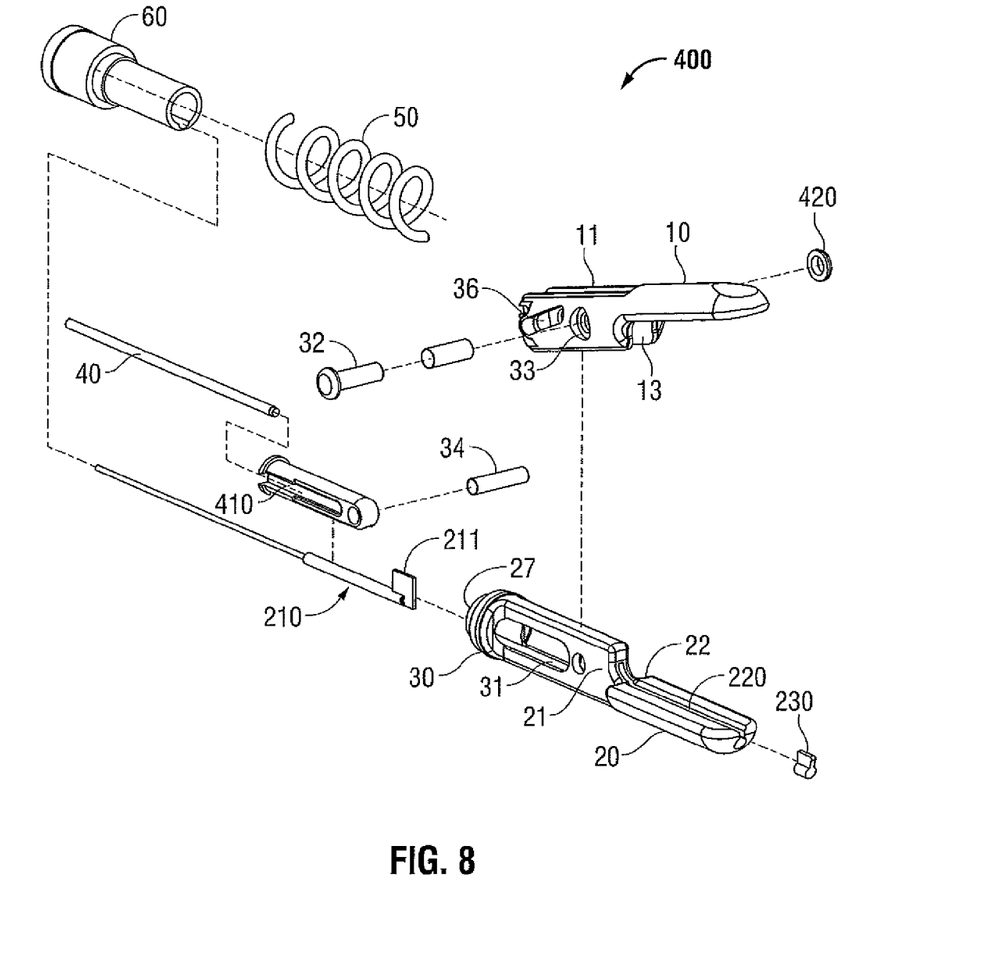
FIG. 8 is an exploded view of the end effector assembly of FIG. 6 with parts separated, in accordance with the present disclosure.

Referring to FIGS. 7 and 8, exploded views 300, 400 of end effector assemblies 100, 200 of FIGS. 3 and 6, respectively, are presented.

FIG. 7 additionally includes camming member 310 that is received by supporting member 30, as well as washer 320 that secures pivot pin 32 to first jaw member 10. The camming member 310 is slidably received in cavity 27 to allow for the reception of cam pin 34. Moreover, jaw flange 21 houses a channel 31 for cam pin 34 to ride on. In other words, the jaw flange 21 is configured to allow reception of the cam pin 34. Thus, the cam pin 34 supports camming member 310 in a cuff-like manner. As a result, a constant closure force is applied, such that the camming member 310 moves with the cam pin 34, the cam pin 34 moving within the cam surface. When the cam pin 34 moves back, it causes the jaw member 10 to slide down to clamp tissue. Furthermore, opening 11 of jaw member 10 is bifurcated to define cavity 13 therebetween and configured to encompass flange 21 of the second jaw member 20.

FIG. 8 additionally includes camming member 410 that is received by supporting member 30, as well as washer 420 that secures pivot pin 32 to first jaw member 10. Similarly to FIG. 7, the camming member 410 is slidably received in cavity 27 to allow for the reception of cam pin 34. Moreover, jaw flange 21 houses a channel 31 for cam pin 34 to ride on. In other words, the jaw flange 21 is configured to allow reception of the cam pin 34. Thus, the cam pin 34 supports camming member 410 in a cuff-like manner. As a result, a constant closure force is applied, such that the camming member 410 moves with the cam pin 34, the cam pin 34 moving within the cam surface. When the cam pin 34 moves back, it causes the jaw member 10 to slide down to clamp tissue. Furthermore, opening 11 of jaw member 10 is bifurcated to define cavity 13 therebetween and configured to encompass flange 21 of the second jaw member 20.

In an alternate embodiment, jaw members 10, 20 may be curved in order to reach specific anatomical structures. For example, jaw members 10, 20 may be configured at an angle of about 50 degrees to about 70 degrees for accessing and sealing specific anatomical structures relevant to prostatectomies and cystectomies, e.g., the dorsal vein complex and the lateral pedicles.

Moreover, the instrument(s) of the present disclosure may be constructed to be disposable or alternatively reposable. Accordingly, to make the instrument(s) as inexpensively as possible most of the components are made of a plastic material. End effector assemblies 100, 200, and 500 are designed such that they are fully or partially disposable depending upon a particular purpose or to achieve a particular result. For example, end effector assemblies 100, 200, and 500 may be selectively and releasably engageable with the distal end of elongated shaft 60 attached to a catheter 70 (see FIG. 9). In such an instance, end effector assemblies 100, 200, 500 are considered "partially disposable" or "reposable," i.e., a new or different end effector assembly 100, 200, 500 selectively replaces the old end effector assembly 100, 200, 500 as needed.

From the foregoing and with reference to the various figure drawings, those skilled in the art will appreciate that certain modifications may also be made to the present disclosure without departing from the scope of the same. For example, other spring mechanisms such as, for example, foam, spring washers, bellows and compressed air and so forth, is operably associated with any of the aforementioned jaw components, and utilized to generate a closure or sealing force at the jaw members.

It will be understood that there are to be no limitations as to the dimensions and shape of the jaw members, including the supporting member and spring mechanism, or the materials from which the jaw members and spring mechanism are manufactured or the electronics that are used to run such end effector assembly. It is to be realized that the optimum dimensional relationships for the parts of the present disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly, comprising:
a pair of first and second jaw members configured to move from a first position in spaced relation relative to one another to a second position for grasping tissue therebetween;
an actuation mechanism configured to actuate the first and second jaw members relative to an elongated shaft, the elongated shaft attached to a catheter, and the elongated shaft having a longitudinal axis defined therethrough; and
a spring mechanism having a first end and a second end, the spring mechanism configured to apply constant sealing forces between the first and second jaw members irrespective of angular displacement of the elongated shaft with respect to the longitudinal axis,
wherein the first end of the spring mechanism engages a supporting member configured to secure the first and second jaw members therewith and a second end of the spring mechanism engages a distal end of the elongated shaft.

2. The end effector assembly according to claim 1, wherein the elongated shaft includes an interior defined therein and the spring mechanism is disposed outside of the interior of the elongated shaft.

3. The end effector assembly according to claim 1, wherein the elongated shaft and the catheter are bendable.

4. The end effector assembly according to claim 1, wherein the actuation mechanism includes at least one drive element.

5. The end effector assembly according to claim 1, wherein a cam pin is mounted within the supporting member, which rides on a cam slot in the first jaw member, such that the first jaw member closes with respect to the second jaw member.

6. The end effector assembly according to claim 5, wherein the cam slot is disposed at an angle relative to the longitudinal axis defined by the elongated shaft.

7. The end effector assembly according to claim 5, wherein the actuation mechanism causes a camming member to be slidably received within a cavity of the second jaw member to allow reception of the cam pin.

8. The end effector assembly according to claim 1, wherein the spring mechanism is selected from a group including a coil spring, and a cantilever spring.

9. The end effector assembly according to claim 1, wherein the spring mechanism is rated at less than 120 pounds per square inch.

10. The end effector assembly according to claim 1, wherein the spring mechanism provides a closure force of about 3 kg/cm$^2$ to about 16 kg/cm$^2$ between the pair of jaw members.

11. The end effector assembly according to claim 1, wherein a tissue contacting surface of one of the first and second jaw members includes a cutting assembly.

12. The end effector assembly according to claim 11, wherein a second actuation mechanism actuates the cutting assembly to slidingly advance across the tissue contacting surface of the second jaw member along the longitudinal axis defined by the elongated shaft to cut tissue disposed between the pair of jaw members.

13. An end effector assembly, comprising:
a pair of first and second jaw members configured to move from a first position in spaced relation relative to one another to a second position for grasping tissue therebetween;
an actuation mechanism configured to actuate the first and second jaw members relative to an elongated shaft, the elongated shaft attached to a catheter, and the elongated shaft having a longitudinal axis defined therethrough;
a spring mechanism having a first end and a second end, the spring mechanism configured to apply constant sealing forces between the first and second jaw members irrespective of angular displacement of the elongated shaft with respect to the longitudinal axis; and
a cam slot configured to cooperate with the supporting member to receive a cam pin therethrough,
wherein the first end of the spring mechanism engages a supporting member configured to secure the first and second jaw members therewith and a second end of the spring mechanism engages a distal end of the elongated shaft.

14. The end effector assembly according to claim 13, wherein the elongated shaft includes an interior defined therein and the spring mechanism is disposed outside of the interior of the elongated shaft.

15. The end effector assembly according to claim 13, wherein the elongated shaft and the catheter are bendable.

16. The end effector assembly according to claim 13, wherein the actuation mechanism includes at least one drive element.

17. The end effector assembly according to claim 13, wherein the spring mechanism is selected from a group including a coil spring, and a cantilever spring.

18. The end effector assembly according to claim 13, wherein the spring mechanism is rated at less than 120 pounds per square inch.

19. The end effector assembly according to claim 13, wherein a tissue contacting surface of one of the first and second jaw members includes a cutting assembly.

20. The end effector assembly according to claim 19, wherein a second actuation mechanism actuates the cutting assembly to slidingly advance across the tissue contacting surface of the second jaw member along the longitudinal axis defined by the elongated shaft to cut tissue disposed between the pair of jaw members.

* * * * *